(12) United States Patent
Wong et al.

(10) Patent No.: US 9,133,835 B2
(45) Date of Patent: Sep. 15, 2015

(54) CONTROLLING OF MULTIPLE PUMPS

(71) Applicant: Abbott Medical Optics Inc., Santa Ana, CA (US)

(72) Inventors: Wayne Wong, Irvine, CA (US); Dan A Peters, Temecula, CA (US); Timothy Hunter, Irvine, CA (US); William J Ade, Vista, CA (US); Keith T Handa, San Clemente, CA (US)

(73) Assignee: Abbott Medical Optics Inc., Santa Ana, CA (US)

( * ) Notice: Subject to any disclaimer, the term of this patent is extended or adjusted under 35 U.S.C. 154(b) by 237 days.

(21) Appl. No.: 13/854,661

(22) Filed: Apr. 1, 2013

(65) Prior Publication Data

US 2014/0133998 A1      May 15, 2014

Related U.S. Application Data

(63) Continuation of application No. 12/613,567, filed on Nov. 6, 2009, now Pat. No. 8,409,155.

(60) Provisional application No. 61/112,620, filed on Nov. 7, 2008.

(51) Int. Cl.
   *F04B 23/08* (2006.01)
   *A61F 9/007* (2006.01)
   (Continued)

(52) U.S. Cl.
   CPC ............. *F04B 23/08* (2013.01); *A61F 9/00745* (2013.01); *F04B 49/00* (2013.01); *G05G 1/445* (2013.01); *A61M 1/0031* (2013.01); *A61M 2205/078* (2013.01)

(58) Field of Classification Search
   CPC .................... A61B 2017/00973; A61F 9/007; A61M 1/0031; A61M 1/0058; A61M 2205/078; A61M 2210/0612

USPC ............................................ 604/35, 118, 119
See application file for complete search history.

(56) References Cited

U.S. PATENT DOCUMENTS

| 1,848,024 A | 3/1932 | Owen |
| 2,123,781 A | 7/1938 | Huber |

(Continued)

FOREIGN PATENT DOCUMENTS

| AU | 2006235983 A1 | 5/2007 |
| DE | 3826414 A1 | 2/1989 |

(Continued)

OTHER PUBLICATIONS

Boyd, "Preparing for the Transition" in: The Art and the Science of Cataract Surgery, Chapter 7, 2011, pp. 93-133.

(Continued)

*Primary Examiner* — Gerald Landry, II
(74) *Attorney, Agent, or Firm* — Abbott Medical Optics Inc.

(57) ABSTRACT

An apparatus for controlling vacuum pressure is provided. The apparatus includes a multiple axis controller, such as a dual axis footpedal, and a processing apparatus, such as an instrument host running software, configured to receive multiple axis data from the multiple axis controller. The apparatus also includes a first pump configured to provide nonzero fluid pressure at a first nonzero fluid pressure level based on a first axis state of the multiple axis controller and a second pump configured to provide nonzero fluid pressure at a second nonzero fluid pressure level based on a second axis state of the multiple axis controller. The processing apparatus causes switching between the first pump and the second pump based on the first axis state and the second axis state of the multiple axis controller.

28 Claims, 6 Drawing Sheets

(51) Int. Cl.
*G05G 1/445* (2008.04)
*F04B 49/00* (2006.01)
*A61M 1/00* (2006.01)

(56) References Cited

U.S. PATENT DOCUMENTS

| | | | |
|---|---|---|---|
| 3,076,904 A | 2/1963 | Claus et al. |
| 3,116,697 A | 1/1964 | Theodore |
| 3,439,680 A | 4/1969 | Thomas, Jr. |
| 3,526,219 A | 9/1970 | Lewis |
| 3,781,142 A | 12/1973 | Zweig |
| 3,857,387 A | 12/1974 | Shock |
| 4,017,828 A | 4/1977 | Watanabe et al. |
| 4,037,491 A | 7/1977 | Newbold |
| 4,189,286 A | 2/1980 | Murry et al. |
| 4,193,004 A | 3/1980 | Lobdell et al. |
| 4,276,023 A | 6/1981 | Phillips et al. |
| 4,537,561 A | 8/1985 | Xanthopoulos |
| 4,564,342 A | 1/1986 | Weber et al. |
| 4,590,934 A | 5/1986 | Malis et al. |
| 4,665,621 A | 5/1987 | Ackerman et al. |
| 4,706,687 A | 11/1987 | Rogers et al. |
| 4,757,814 A | 7/1988 | Wang et al. |
| 4,758,220 A | 7/1988 | Sundblom et al. |
| 4,772,263 A | 9/1988 | Dorman et al. |
| 4,773,897 A | 9/1988 | Scheller et al. |
| 4,818,186 A | 4/1989 | Pastrone et al. |
| 4,837,857 A | 6/1989 | Scheller et al. |
| 4,920,336 A | 4/1990 | Meijer |
| 4,921,477 A | 5/1990 | Davis |
| 4,933,843 A | 6/1990 | Scheller et al. |
| 4,954,960 A | 9/1990 | Lo et al. |
| 4,961,424 A | 10/1990 | Kubota et al. |
| 4,965,417 A | 10/1990 | Massie |
| 4,983,901 A | 1/1991 | Lehmer |
| 4,998,972 A | 3/1991 | Chin et al. |
| 5,006,110 A | 4/1991 | Garrison et al. |
| 5,020,535 A | 6/1991 | Parker et al. |
| 5,026,387 A | 6/1991 | Thomas |
| 5,039,973 A | 8/1991 | Carballo |
| 5,091,656 A | 2/1992 | Gahn |
| 5,108,367 A | 4/1992 | Epstein et al. |
| 5,110,270 A | 5/1992 | Morrick |
| 5,125,891 A | 6/1992 | Hossain et al. |
| 5,160,317 A | 11/1992 | Costin |
| 5,195,960 A | 3/1993 | Hossain et al. |
| 5,195,961 A | 3/1993 | Takahashi et al. |
| 5,195,971 A | 3/1993 | Sirhan |
| 5,230,614 A | 7/1993 | Zanger et al. |
| 5,249,121 A | 9/1993 | Baum et al. |
| 5,268,624 A | 12/1993 | Zanger |
| 5,271,379 A | 12/1993 | Phan et al. |
| 5,282,787 A | 2/1994 | Wortrich |
| 5,323,543 A | 6/1994 | Steen et al. |
| 5,342,293 A | 8/1994 | Zanger |
| 5,350,357 A | 9/1994 | Kamen et al. |
| 5,351,676 A | 10/1994 | Putman |
| 5,388,569 A | 2/1995 | Kepley |
| 5,454,783 A | 10/1995 | Grieshaber et al. |
| 5,464,391 A | 11/1995 | DeVale |
| 5,470,211 A | 11/1995 | Knott et al. |
| 5,470,312 A | 11/1995 | Zanger et al. |
| 5,499,969 A | 3/1996 | Beuchat et al. |
| 5,520,652 A | 5/1996 | Peterson |
| 5,533,976 A | 7/1996 | Zaleski et al. |
| 5,549,461 A | 8/1996 | Newland |
| 5,554,894 A | 9/1996 | Sepielli |
| 5,561,575 A | 10/1996 | Eways |
| 5,569,188 A | 10/1996 | Mackool |
| 5,580,347 A | 12/1996 | Reimels |
| 5,591,127 A | 1/1997 | Barwick, Jr. et al. |
| 5,653,887 A | 8/1997 | Wahl et al. |
| 5,657,000 A | 8/1997 | Ellingboe |
| 5,676,530 A | 10/1997 | Nazarifar |
| 5,676,649 A | 10/1997 | Boukhny et al. |
| 5,676,650 A | 10/1997 | Grieshaber et al. |
| 5,693,020 A | 12/1997 | Rauh |
| 5,697,898 A | 12/1997 | Devine |
| 5,697,910 A | 12/1997 | Cole et al. |
| 5,700,240 A | 12/1997 | Barwick, Jr. et al. |
| 5,724,264 A | 3/1998 | Rosenberg et al. |
| 5,728,130 A | 3/1998 | Ishikawa et al. |
| 5,733,256 A | 3/1998 | Costin |
| 5,745,647 A | 4/1998 | Krause |
| 5,747,824 A | 5/1998 | Jung et al. |
| 5,777,602 A | 7/1998 | Schaller et al. |
| 5,805,998 A | 9/1998 | Kodama |
| 5,807,075 A | 9/1998 | Jacobsen et al. |
| 5,830,176 A | 11/1998 | Mackool |
| 5,843,109 A | 12/1998 | Mehta et al. |
| 5,859,642 A | 1/1999 | Jones |
| 5,871,492 A | 2/1999 | Sorensen |
| 5,879,298 A | 3/1999 | Drobnitzky et al. |
| 5,883,615 A | 3/1999 | Fago et al. |
| 5,899,674 A | 5/1999 | Jung et al. |
| 5,928,257 A | 7/1999 | Kablik et al. |
| 5,983,749 A | 11/1999 | Holtorf |
| 6,002,484 A | 12/1999 | Rozema et al. |
| 6,024,428 A | 2/2000 | Uchikata |
| 6,062,829 A | 5/2000 | Ognier |
| 6,077,285 A | 6/2000 | Boukhny |
| 6,086,598 A | 7/2000 | Appelbaum et al. |
| 6,109,895 A | 8/2000 | Ray et al. |
| 6,117,126 A | 9/2000 | Appelbaum et al. |
| 6,139,320 A | 10/2000 | Hahn |
| 6,150,623 A | 11/2000 | Chen |
| 6,179,829 B1 * | 1/2001 | Bisch et al. ............. 606/1 |
| 6,219,032 B1 | 4/2001 | Rosenberg et al. |
| 6,251,113 B1 | 6/2001 | Appelbaum et al. |
| 6,260,434 B1 | 7/2001 | Holtorf |
| 6,360,630 B2 | 3/2002 | Holtorf |
| 6,368,269 B1 | 4/2002 | Lane |
| 6,411,062 B1 | 6/2002 | Baranowski et al. |
| 6,424,124 B2 | 7/2002 | Ichihara et al. |
| 6,436,072 B1 | 8/2002 | Kullas et al. |
| 6,452,120 B1 | 9/2002 | Chen |
| 6,452,123 B1 | 9/2002 | Chen |
| 6,491,661 B1 | 12/2002 | Boukhny et al. |
| 6,511,454 B1 | 1/2003 | Nakao et al. |
| 6,537,445 B2 | 3/2003 | Muller |
| 6,595,948 B2 | 7/2003 | Suzuki et al. |
| 6,632,214 B2 | 10/2003 | Morgan et al. |
| 6,674,030 B2 | 1/2004 | Chen et al. |
| 6,830,555 B2 | 12/2004 | Rockley et al. |
| 6,852,092 B2 | 2/2005 | Kadziauskas et al. |
| 6,862,951 B2 | 3/2005 | Peterson et al. |
| 6,908,451 B2 | 6/2005 | Brody et al. |
| 6,962,488 B2 | 11/2005 | Davis et al. |
| 6,962,581 B2 | 11/2005 | Thoe |
| 7,011,761 B2 | 3/2006 | Muller |
| 7,012,203 B2 | 3/2006 | Hanson et al. |
| 7,070,578 B2 | 7/2006 | Leukanech et al. |
| 7,073,083 B2 | 7/2006 | Litwin, Jr. et al. |
| 7,087,049 B2 | 8/2006 | Nowlin et al. |
| 7,103,344 B2 | 9/2006 | Menard |
| 7,167,723 B2 | 1/2007 | Zhang |
| 7,169,123 B2 | 1/2007 | Kadziauskas et al. |
| 7,236,766 B2 | 6/2007 | Freeburg |
| 7,236,809 B2 | 6/2007 | Fischedick et al. |
| 7,242,765 B2 | 7/2007 | Hairston |
| 7,244,240 B2 | 7/2007 | Nazarifar et al. |
| 7,289,825 B2 | 10/2007 | Fors et al. |
| 7,300,264 B2 | 11/2007 | Souza |
| 7,316,664 B2 | 1/2008 | Kadziauskas et al. |
| 7,336,976 B2 | 2/2008 | Ito |
| 7,381,917 B2 | 6/2008 | Dacquay et al. |
| 7,439,463 B2 | 10/2008 | Brenner et al. |
| 7,465,285 B2 | 12/2008 | Hutchinson et al. |
| 7,470,277 B2 | 12/2008 | Finlay et al. |
| 7,526,038 B2 | 4/2009 | McNamara |
| 7,591,639 B2 | 9/2009 | Kent |
| 7,731,484 B2 | 6/2010 | Yamamoto et al. |
| 7,776,006 B2 | 8/2010 | Childers et al. |
| 7,811,255 B2 * | 10/2010 | Boukhny et al. ............. 604/118 |

(56) References Cited

U.S. PATENT DOCUMENTS

| | | |
|---|---|---|
| 7,883,521 B2 | 2/2011 | Rockley et al. |
| 7,921,017 B2 | 4/2011 | Claus et al. |
| 7,967,777 B2 | 6/2011 | Edwards et al. |
| 8,070,712 B2 | 12/2011 | Muri et al. |
| 8,075,468 B2 | 12/2011 | Min et al. |
| 2001/0023331 A1 | 9/2001 | Kanda et al. |
| 2001/0047166 A1 | 11/2001 | Wuchinich |
| 2001/0051788 A1 | 12/2001 | Paukovits et al. |
| 2002/0019215 A1 | 2/2002 | Romans |
| 2002/0019607 A1 | 2/2002 | Bui |
| 2002/0045887 A1 | 4/2002 | DeHoogh et al. |
| 2002/0070840 A1 | 6/2002 | Fischer et al. |
| 2002/0098859 A1 | 7/2002 | Murata |
| 2002/0137007 A1 | 9/2002 | Beerstecher |
| 2002/0179462 A1 | 12/2002 | Silvers |
| 2003/0073980 A1 | 4/2003 | Finlay et al. |
| 2003/0083016 A1 | 5/2003 | Evans et al. |
| 2003/0108429 A1 | 6/2003 | Angelini et al. |
| 2003/0125717 A1 | 7/2003 | Whitman |
| 2003/0224729 A1 | 12/2003 | Arnold |
| 2003/0226091 A1 | 12/2003 | Platenberg et al. |
| 2004/0037724 A1 | 2/2004 | Haser et al. |
| 2004/0068300 A1 | 4/2004 | Kadziauskas et al. |
| 2004/0092922 A1 | 5/2004 | Kadziauskas et al. |
| 2004/0193182 A1 | 9/2004 | Yaguchi et al. |
| 2004/0212344 A1 | 10/2004 | Tamura et al. |
| 2004/0215127 A1 | 10/2004 | Kadziauskas et al. |
| 2004/0224641 A1 | 11/2004 | Sinn |
| 2004/0253129 A1 | 12/2004 | Sorensen et al. |
| 2005/0054971 A1 | 3/2005 | Steen et al. |
| 2005/0065462 A1 | 3/2005 | Nazarifar et al. |
| 2005/0069419 A1 | 3/2005 | Cull et al. |
| 2005/0070859 A1 | 3/2005 | Cull et al. |
| 2005/0095153 A1 | 5/2005 | Demers et al. |
| 2005/0109595 A1 | 5/2005 | Mezhinsky et al. |
| 2005/0118048 A1 | 6/2005 | Traxinger |
| 2005/0130098 A1 | 6/2005 | Warner |
| 2005/0187513 A1 | 8/2005 | Rabiner et al. |
| 2005/0197131 A1 | 9/2005 | Ikegami |
| 2005/0209560 A1 | 9/2005 | Boukhny et al. |
| 2005/0236936 A1 | 10/2005 | Shiv et al. |
| 2005/0245888 A1 | 11/2005 | Cull |
| 2005/0261628 A1 | 11/2005 | Boukhny et al. |
| 2006/0035585 A1 | 2/2006 | Washiro |
| 2006/0036180 A1 | 2/2006 | Boukhny et al. |
| 2006/0041220 A1 | 2/2006 | Boukhny et al. |
| 2006/0046659 A1 | 3/2006 | Haartsen et al. |
| 2006/0078448 A1 | 4/2006 | Holden |
| 2006/0145540 A1 | 7/2006 | Mezhinsky |
| 2006/0219049 A1 | 10/2006 | Horvath et al. |
| 2006/0219962 A1 | 10/2006 | Dancs et al. |
| 2006/0224107 A1 | 10/2006 | Claus et al. |
| 2006/0236242 A1 | 10/2006 | Boukhny et al. |
| 2007/0016174 A1 | 1/2007 | Millman et al. |
| 2007/0049898 A1 | 3/2007 | Hopkins et al. |
| 2007/0060926 A1 | 3/2007 | Escaf |
| 2007/0073214 A1 | 3/2007 | Dacquay et al. |
| 2007/0073309 A1 | 3/2007 | Kadziauskas et al. |
| 2007/0078379 A1 | 4/2007 | Boukhny et al. |
| 2007/0249942 A1 | 10/2007 | Salehi et al. |
| 2008/0033342 A1 | 2/2008 | Staggs |
| 2008/0066542 A1 | 3/2008 | Gao |
| 2008/0067046 A1 | 3/2008 | Dacquay et al. |
| 2008/0112828 A1 | 5/2008 | Muri et al. |
| 2008/0114289 A1 | 5/2008 | Muri et al. |
| 2008/0114290 A1 | 5/2008 | King et al. |
| 2008/0114291 A1 | 5/2008 | Muri et al. |
| 2008/0114300 A1 | 5/2008 | Muri et al. |
| 2008/0114311 A1 | 5/2008 | Muri et al. |
| 2008/0114312 A1 | 5/2008 | Muri et al. |
| 2008/0114372 A1 | 5/2008 | Edwards et al. |
| 2008/0114387 A1* | 5/2008 | Hertweck et al. ............ 606/170 |
| 2008/0125695 A1 | 5/2008 | Hopkins et al. |
| 2008/0125697 A1* | 5/2008 | Gao ............................... 604/35 |
| 2008/0125698 A1 | 5/2008 | Gerg et al. |
| 2008/0146989 A1 | 6/2008 | Zacharias |
| 2008/0243105 A1 | 10/2008 | Horvath |
| 2008/0262476 A1 | 10/2008 | Krause et al. |
| 2008/0281253 A1 | 11/2008 | Injev et al. |
| 2008/0294087 A1 | 11/2008 | Steen et al. |
| 2008/0312594 A1 | 12/2008 | Urich et al. |
| 2009/0005712 A1 | 1/2009 | Raney |
| 2009/0005789 A1 | 1/2009 | Charles |
| 2009/0048607 A1* | 2/2009 | Rockley ........................ 606/107 |
| 2009/0124974 A1* | 5/2009 | Crank et al. .................. 604/118 |
| 2009/0163853 A1 | 6/2009 | Cull et al. |
| 2010/0185150 A1 | 7/2010 | Zacharias |
| 2010/0280435 A1 | 11/2010 | Raney et al. |
| 2011/0092887 A1 | 4/2011 | Wong et al. |
| 2011/0092924 A1 | 4/2011 | Wong et al. |
| 2011/0092962 A1 | 4/2011 | Ma et al. |
| 2011/0098721 A1 | 4/2011 | Tran et al. |
| 2011/0160646 A1 | 6/2011 | Kadziauskas et al. |
| 2012/0065580 A1 | 3/2012 | Gerg et al. |

FOREIGN PATENT DOCUMENTS

| | | |
|---|---|---|
| EP | 56019 A1 | 7/1982 |
| EP | 619993 A1 | 10/1994 |
| EP | 1010437 A1 | 6/2000 |
| EP | 1072285 A1 | 1/2001 |
| EP | 1113562 A1 | 7/2001 |
| EP | 1310267 A2 | 5/2003 |
| EP | 1469440 A2 | 10/2004 |
| EP | 1550406 A2 | 7/2005 |
| EP | 1704839 A1 | 9/2006 |
| EP | 1779879 A1 | 5/2007 |
| EP | 1787606 A1 | 5/2007 |
| EP | 1849443 A1 | 10/2007 |
| EP | 1849444 A1 | 10/2007 |
| EP | 1857128 A1 | 11/2007 |
| EP | 1867349 A1 | 12/2007 |
| EP | 1310267 B1 | 1/2008 |
| EP | 1873501 A1 | 1/2008 |
| EP | 1900347 A1 | 3/2008 |
| EP | 1925274 A2 | 5/2008 |
| EP | 1867349 B1 | 11/2008 |
| ES | 2264369 A1 | 12/2006 |
| GB | 2230301 A | 10/1990 |
| GB | 2352887 A | 2/2001 |
| JP | 57024482 A | 2/1982 |
| JP | 2008188110 A | 8/2008 |
| WO | 9220310 A1 | 11/1992 |
| WO | WO-9315777 A2 | 8/1993 |
| WO | 9317729 A1 | 9/1993 |
| WO | 9324082 A1 | 12/1993 |
| WO | WO-9405346 A1 | 3/1994 |
| WO | 9632144 A1 | 10/1996 |
| WO | 9818507 A1 | 5/1998 |
| WO | 9917818 A1 | 4/1999 |
| WO | 0000096 A1 | 1/2000 |
| WO | 0070225 A1 | 11/2000 |
| WO | WO-0122696 A1 | 3/2001 |
| WO | WO-0228449 A2 | 4/2002 |
| WO | 0234314 A1 | 5/2002 |
| WO | WO-03102878 A1 | 12/2003 |
| WO | WO-2004096360 A1 | 11/2004 |
| WO | WO-2004114180 A1 | 12/2004 |
| WO | 2005084728 A2 | 9/2005 |
| WO | 2005092023 A2 | 10/2005 |
| WO | 2005092047 A2 | 10/2005 |
| WO | 2006101908 A2 | 9/2006 |
| WO | 2006125280 A1 | 11/2006 |
| WO | 2007121144 A1 | 10/2007 |
| WO | 2007143677 A2 | 12/2007 |
| WO | 2007143797 A1 | 12/2007 |
| WO | WO-2007149637 A2 | 12/2007 |
| WO | 2008030872 A1 | 3/2008 |
| WO | 2008060859 A1 | 5/2008 |
| WO | 2008060902 A1 | 5/2008 |
| WO | 2008060995 A1 | 5/2008 |
| WO | 2010054146 A1 | 5/2010 |

(56) References Cited

FOREIGN PATENT DOCUMENTS

WO          2010054225 A2    5/2010
WO    WO-2013142009 A1    9/2013

OTHER PUBLICATIONS

Co-pending U.S. Appl. No. 13/922,475, filed Jun. 20, 2013.
English Human Translation of JP57024482 from Feb. 9, 1982.
International Preliminary Report on Patentability and Written Opinion for Application No. PCT/US07/083875, mailed on May 12, 2009, 8 pages.
International Preliminary Report on Patentability and Written Opinion for Application No. PCT/US07/084157, mailed on May 12, 2009, 10 pages.
International Search Report for Application No. PCT/US07/083875, mailed on May 7, 2008, 4 pages.
International Search Report for Application No. PCT/US07/083880, mailed on May 30, 2008, 4 pages.
International Search Report for Application No. PCT/US07/084157, mailed on Apr. 1, 2008, 3 pages.
International Search Report for Application No. PCT/US07/084163, mailed on Apr. 1, 2008, 3 pages.
International Search Report for Application No. PCT/US08/064240, mailed on Oct. 29, 2008, 3 pages.
International Search Report for Application No. PCT/US08/071704, mailed on Nov. 26, 2008, 3 pages.
International Search Report for Application No. PCT/US08/072974, mailed on Feb. 23, 2009, 2 pages.
International Search Report for Application No. PCT/US2009/052473, mailed on Nov. 2, 2009, 3 pages.
Phacoemulsification. Oct. 12, 2006. Wikipedia.com. Jun. 19, 2009 <http://en.wikipedia.org/wiki/Phacoemulsification>.
Definition of "Parameter", Retrieved from the Internet:<URL: http://dictionary.reference.com/browse/parameter>.
European Search Report for Application No. EP10164058, mailed on Jun. 25, 2010, 2 pages.
European Search Report for Application No. EP13184138.9, mailed on Oct. 24, 2013. 7 pages.
Examination Report mailed Mar. 28, 2012 for European Applicaitn No. EP097914072 filed Jul. 31, 2009, 3 pages.
International Preliminary Report on Patentability and Written Opinion for Application No. PCT/US07/083880, mailed on May 12, 2009, 7 pages.
International Preilmmary Report on Patentability and Written Opinion for Application No. PCT/US07/084163, mailed on May 12, 2009, 8 pages.
International Preliminary Report on Patentability and Written Opinion for Application No. PCT/US08/064240, mailed on Nov. 24, 2009, 7 pages.
International Preliminary Report on Patentability and Written Opinion for Application No. PCT/US2006/38978, mailed on Apr. 16, 2008, 8 pages.
International Preliminary Report on Patentability and Written Opinion for Application No. PCT/US2006/39868, mailed on Apr. 16, 2008, 6 pages.
International Preliminary Report on Patentability and Written Opinion for Application No. PCT/US2008/072974, mailed on Feb. 16, 2010, 6 pages.
International Preliminary Report on Patentability and Written Opinion for Application No. PCT/US2009/052473, mailed on Feb. 1, 2011, 7 pages.
International Preliminary Report on Patentability and Written Oninion for Application No. PCT/US2009/063479, mailed on May 10, 2011, 11 pages.
International Preliminary Report on Patentability and Written Opinion for Application No. PCT/US2009/063589, mailed on May 10, 2011, 12 pages.
International Search Report and Written Opinion for Application No. PCT/US2014/047055, mailed on Oct. 17, 2014, 11 pages.
International Search Report and Written Opinion, mailed Mar. 2, 2010, and International Preliminary Report on Patentability, mailed May 10, 2011, for Application No. PCT/US2009/063482, 13 pages.
International Search Report and Written Opinion, mailed Nov. 2, 2009, and International Preliminary Report on Patentability, mailed Feb. 1, 2011, for Application No. PCT/US2009/052466, 12 pages.
International Search Report and Written Opinion, mailed May 10, 2010, and International Preliminary Report on Patentability, mailed May 10, 2011, for Application No. PCT/US2009/063569, 17 pages.
International Search Report and Written Opinion, mailed Feb. 11, 2010, and International Preliminary Report on Patentability, mailed May 10, 2011, for Application No. PCT/US2009/063486, 13 pages.
International Search Report for Application No. PCT/US2006/38978, mailed on Feb. 27, 2007, 3 pages.
International Search Report for Application No. PCT/US2006/39868, mailed on Nov. 12, 2007, 3 pages.
International Search Report for Application No. PCT/US2009/063479, mailed Jun. 11, 2010, 5 pages.
International Search Report for Application No. PCT/US2009/063589, mailed on Jul. 21, 2010, 7 pages.
International Search Report for Application No. PCT/US2013/027728, mailed Jul. 31, 2013, 9 pages.
Merritt R., et al., Wireless Nets Starting to link Medical Gear [online] 2004 [retrieved on Feb. 12, 2007]. Retrieved from the Internet: <http://WWW.embedded,com/news/embeddedindustry/17200577?_requestid=174370>.

\* cited by examiner

CONTROLLING OF MULTIPLE PUMPS

CROSS-REFERENCE TO RELATED APPLICATIONS

This application claims priority to and is a continuation of U.S. patent application Ser. No. 12/613,567, filed on Nov. 6, 2009, which claims the benefit of U.S. Provisional Application No. 61/112,620, filed on Nov. 7, 2008, the entirety of both of which are hereby incorporated by reference.

BACKGROUND OF THE INVENTION

1. Field of the Invention

The present invention relates generally to ocular surgery, and more specifically to controlling multiple pumps in a medical system, such as a phacoemulsification system, configured for concurrent operation from a footpedal during ophthalmic surgical procedures.

2. Description of the Related Art

Phacoemulsification surgery has been successfully employed in the treatment of certain ocular issues, such as removal of a cataract-damaged lens and implantation of an intraocular lens. Phacoemulsification surgery typically involves removal of the cataract-damaged lens utilizing a small incision at the edge of the cornea. Through the small incision, the surgeon then creates an opening in the capsule, i.e. membrane that encapsulates the lens.

The surgeon can insert an ultrasonic probe, incorporated within a phacoemulsification handpiece, through the opening in the cornea and capsule, thus accessing the damaged lens. The handpiece's ultrasonically actuated tip emulsifies the damaged lens such that the lens can be evacuated by the handpiece. After the damaged natural lens is completely removed, the handpiece tip is withdrawn from the eye. The surgeon may now implant an intraocular lens into the space made available in the capsule.

Today's fluidic-based systems typically use various pumps, and frequently employ two general types of pumps for aspirating lens material. A flow based fluidic system, operating a peristaltic/scroll pump, generates vacuum when the aspirating tip becomes occluded/blocked. A vacuum based fluidic system, operating a venturi/rotary vane pump generates vacuum though air pressure using either an internal or external air source and a reservoir. Multiple pump systems are being employed in current phacoemulsification devices, and other types or styles of pumps can be employed beyond the aforementioned peristaltic and venturi pumps.

While performing phacoemulsification surgical techniques, such as lens removal, a surgeon may wish to employ either a flow based pump or vacuum based pump to irrigate and aspirate the eye. Current designs limit the surgeon/operator to selecting between flow or vacuum based functionality, unable to provide for operating both flow and vacuum based systems concurrently or sequentially using a single software application and controller, such as a footpedal.

Previously available fluidic-based designs typically provided for operation of a single pump within the controlling software application. If the surgeon determines during the procedure a need to switch from, for example, flow to vacuum based functionality, the surgeon has been required to change or switch sub-mode operation within the software application to affect the desired aspiration source type. Switching sub-mode operation in this manner took time to switch between pumps and tends to be unwieldy during operations.

In a situation where the surgeon/operator manually switches pumps, the transition from, for example, flow based operation to vacuum based operation over a period of time may introduce undesirable ocular chamber instability during the transition. Instability results from the transition time switching between pumps, as such a lag may result in a loss of pressure in the eye and/or fluid flowing out of the eye, both highly undesirable occurrences.

Based on the foregoing, it would be beneficial to offer a design for seamlessly switching between multiple aspiration pumps when using an ultrasonic handpiece in an ocular surgical procedure that overcomes drawbacks present in previously known designs.

SUMMARY OF THE INVENTION

According to a first aspect of the present design, there is provided a method for operating two pressure sources. The method comprises activating a first pump using a multiple channel adjustment apparatus, such as a dual axis footpedal, configured to operate with the first pump to provide nonzero fluid pressure at a first nonzero fluid pressure level based on a first channel state of the multiple channel adjustment apparatus. The method also comprises transitioning from the first pump providing nonzero fluid pressure at the first nonzero fluid pressure level to a second pump providing nonzero fluid pressure at a second nonzero fluid pressure level using the multiple channel adjustment apparatus based on the first channel state and a second channel state of the multiple channel adjustment apparatus.

According to a second aspect of the present design, there is provided a method for delivering vacuum, comprising controlling a first pump using a first signal received from a dual axis device, such as a dual axis footpedal, indicating a first axis position, controlling a second pump using a second signal received from the dual axis device indicating a second axis position, and switching from the first pump to the second pump based on the second axis position.

According to a third aspect of the present design, there is provided an apparatus for controlling vacuum pressure. The apparatus comprises a multiple axis controller, such as a dual axis footpedal operable in pitch and yaw, a processing apparatus, such as an instrument host running software, configured to receive multiple axis data from the multiple axis controller. The apparatus also includes a first pump configured to provide nonzero fluid pressure at a first nonzero fluid pressure level based on a first axis state of the multiple axis controller and a second pump configured to provide nonzero fluid pressure at a second nonzero fluid pressure level based on a second axis state of the multiple axis controller. The processing apparatus causes switching between the first pump and the second pump based on the first axis state and the second axis state of the multiple axis controller.

These and other advantages of the present invention will become apparent to those skilled in the art from the following detailed description of the invention and the accompanying drawings.

BRIEF DESCRIPTION OF THE DRAWINGS

The present invention is illustrated by way of example, and not by way of limitation, in the figures of the accompanying drawings in which.

DETAILED DESCRIPTION OF THE INVENTION

Figure 1:
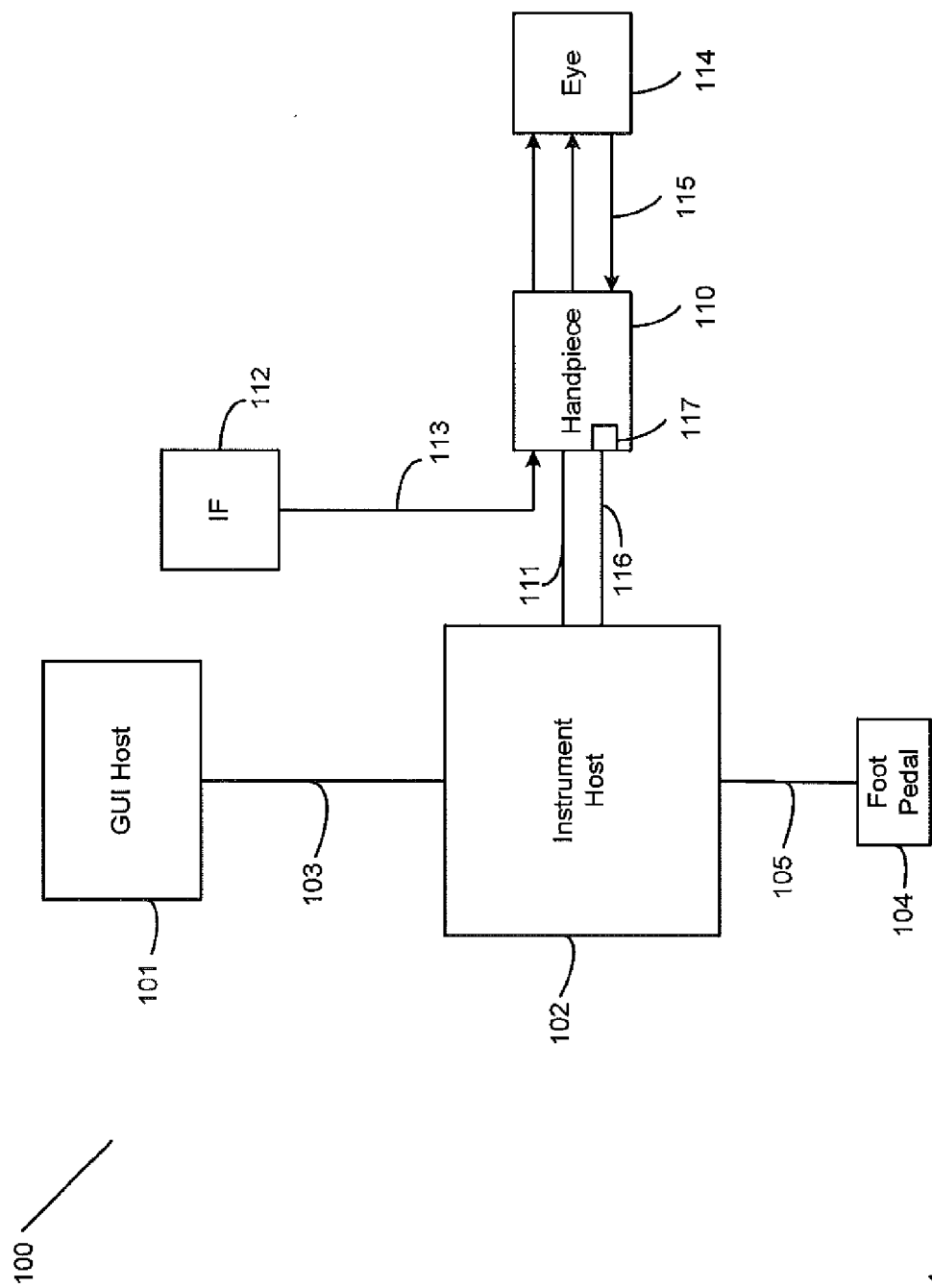
FIG. 1 illustrates an exemplary phacoemulsification/vitrectomy irrigation/aspiration system in a functional block diagram to show the components and interfaces for a safety critical medical instrument system that may be employed in accordance with an aspect of the present invention.

The following description and the drawings illustrate specific embodiments sufficient to enable those skilled in the art to practice the system and method described. Other embodiments may incorporate structural, logical, process and other changes. Examples merely typify possible variations. Individual components and functions are generally optional unless explicitly required, and the sequence of operations may vary. Portions and features of some embodiments may be included in or substituted for those of others.

The present design is directed to operating an ultrasonic handpiece during an ocular procedure that entails controlling switching between multiple pumps and multiple pump types, such as from a flow to a vacuum based system or vice versa, and running two or more pumps at the same time during a surgical procedure. The present design may integrate operation for both pump types using software arranged for processing input signals received from a device such as a dual linear footpedal, configured to concurrently provide control signals for each pump. For example, the present design's software program may control the first pump by processing a signal received in response to the surgeon pressing the footpedal along one axis, such as the pitch axis. The software may simultaneously control the second pump by processing a signal received in response to the surgeon operating the footpedal along a different or second axis, such as left or right along the yaw axis. Use of this dual controller, here a footpedal, enables the surgeon to command how much pressure comes from one pump relative to the other pump, and enables the surgeon to control multiple pump operation with little, if any, lag or delay.

The present design may provide for controlling activation and deactivation of two different pumps or pump types simultaneously from a single input device, such as a dual linear footpedal. Controlling a primary pump, such as a peristaltic pump, and a secondary pump, such as a venturi pump, using the dual linear footpedal arrangement may allow the surgeon to control one pump while concurrently activating second pump as desired, using a combined footpedal movement in both the pitch and yaw axes.

Furthermore, the present design's software may provide for "ramping up" and "ramping down" pump control when transitioning from a first pump to a second pump, thus addressing each pump's inherent start and stop characteristics, such as lag and rise time or fall time. Ramping functions may provide smooth and relatively seamless transitions when switching between pump types sufficient for mitigating potential chamber instability experienced when using today's currently available designs.

In short, the present design may provide for independent control over two separate pumps with relatively seamless transitions between multiple pump operations, while affording acceptable chamber stability. The dual-linear footpedal arrangement may permit the surgeon to realize vacuum on demand functionality and moderate vacuum levels as desired.

In summary, the present design may provide for independently controlling at least two pumps and operate each pump to provide the flow and/or vacuum rate required to precisely operate the handpiece and remove particles with less lag than encountered in designs previously available.

System Example

While the present design may be used in various environments and applications, it will be discussed herein with a particular emphasis on an environment where a surgeon or health care practitioner performs. For example, one embodiment of the present design is in or with an ocular surgical system that comprises an independent graphical user interface (GUI) host module, an instrument host module, a GUI device, and a controller module, such as a foot switch, to control the surgical system.

FIG. 1 illustrates an exemplary phacoemulsification/vitrectomy system 100 illustrating the components and interfaces for a safety critical medical instrument system. A serial communication cable 103 connects GUI host 101 module and instrument host 102 module for the purposes of controlling the surgical instrument host 102 by GUI host 101. GUI host 101 and instrument host 102, as well as any other component of system 100, may be connected wirelessly. Instrument host 102 may be considered a computational device in the arrangement shown, but other functionality and arrangements are possible.

A switch module associated with foot pedal 104 may transmit control signals relating internal physical and virtual switch position information as input to the instrument host 102 over serial communications cable 105 (although foot pedal 104 may be connected wirelessly). Instrument host 102 may provide a database file system for storing configuration parameter values, programs, and other data saved in a storage device (not shown). In addition, the database file system may be realized on the GUI host 101 or any other subsystem (not shown) that could accommodate such a file system.

The phacoemulsification/vitrectomy system 100 has a handpiece 110 that includes a needle and electrical means, typically a piezoelectric crystal, for ultrasonically vibrating the needle. The instrument host 102 supplies power on line 111 to a phacoemulsification/vitrectomy handpiece 110. An irrigation fluid source 112 can be fluidly coupled to handpiece 110 through line 113. The irrigation fluid and ultrasonic power are applied by handpiece 110 to an eye, or affected area or region, indicated diagrammatically by block 114. Alternatively, the irrigation source may be routed to eye 114 through a separate pathway independent of the handpiece, e.g. via a second handpiece. Aspiration is provided to eye 114 by one or more pumps (not shown), such as a peristaltic pump and/or venturi pump, via the instrument host 102 through lines 115 and 116. The term "pump" as used herein includes, but is not limited to, flow based peristaltic, venturi, and/or other flow or vacuum based pumps. A surgeon/operator may select ultrasonic pulse amplitude either using the handpiece or via the instrument host and GUI host, or by some other means such as a footpedal 104.

The present design is configured to operate with at least two pumps, a first pump such as a peristaltic or flow pump and a second pump such as a venturi or vacuum pump. Two identical types of pumps may be provided as the two pumps. Additional pumps may be provided as long as they can provide pressure and/or vacuum. Either pump may provide vacuum or pressure depending on the operation of the pump, and as used herein, the terms "vacuum", "pressure", "vacuum source" and "vacuum pressure" are used interchangeably, such that a "vacuum source" may be a peristaltic or a venturi pump, a "vacuum pressure source" may be a venturi or a peristaltic pump, and so forth. It is specifically noted that application of vacuum is application of negative pressure while application of pressure is application of positive pressure, and thus as used herein, the phrase "nonzero fluid pressure" means either fluid vacuum (negative fluid pressure) or fluid pressure (positive fluid pressure). The intent is to convey that either positive or negative pressure is applied or emanates from a source, such as a pump, depending on circumstance and arrangement.

Figure 2:
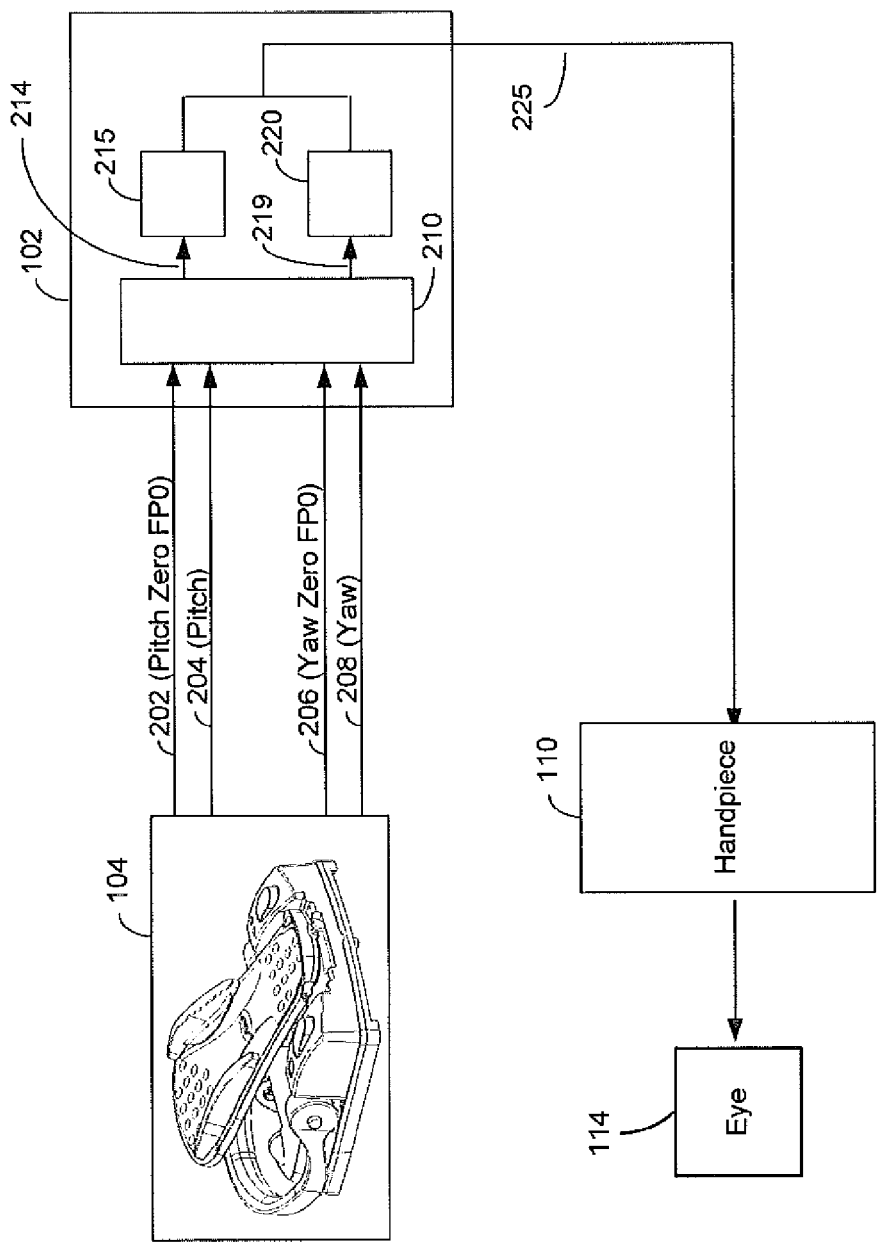
FIG. 2 is a functional block diagram illustrating the multiple aspiration pump control system configured for switching between two different vacuum sources for use in aspirating particles from the patient's eye.

FIG. 2 is a functional block diagram illustrating the multiple pump control (MPC) system configured for switching between two different pumps for use in the ocular surgical procedure. The present design may include a dual linear footpedal 104 or footswitch configured to send signals indicating surgeon/operator movements along two independent linear axes, pitch and yaw. The footpedal 104 signals may include but are not limited to pitch footpedal position zero (FP0) 202, pitch 204, yaw zero (FP0) 206, and yaw 208, where pitch 204 and yaw 208 provide signals for reporting pedal travel in various user-determined operational zones, such as footpedal (FP) zones/positions 1, 2, and 3 (FP1, e.g. irrigation; FP2, e.g. aspiration; and FP3, e.g. ultrasonic power), in each axis of movement.

Signals may be provided from footpedal 104 in the form of counts or a counter monitored by a monitoring device and transmitted to the instrument host 102. For example, the footpedal may read and provide a count over a range representing the movement encountered, such as from zero to 255, with zero representing zero percent movement and 255 representing full (100 percent) movement in, for example, the pitch direction. Yaw zero and pitch zero signals indicate when the yaw and pitch axes are at or about a neutral position or not deflected position, where the neutral position is the position where the footpedal 104 returns when not engaged by a user's foot. Yaw signals may be right and left, such as zero to 255 right and zero to 255 left, or may be from +255 (full right) to −255 (full left) and vice versa. Zones may be defined using the GUI host 101, establishing, for example, zero to 40 percent pitch travel to be FP1, 40 to 80 percent pitch travel to be FP2, and 80 to 100 percent travel to be FP3. More or fewer zones may be employed, and varying ranges may be provided as desired.

The MPC system may include MPC software program 210 configured to receive and process the signals originating from footpedal 109, in the arrangement illustrated, and in turn may provide a first control signal 214 for operating a first pump or pressure/vacuum source, such as peristaltic pump 215, and a second control signal 219 operating a different or second pump or pressure/vacuum source, such as venturi pump 220. The present design may combine the outputs from pumps 215 and 220 and provide for a fluidly connectable output 225 to/from handpiece 110. In this arrangement, the MPC system may provide fluid control for handpiece 110 in accordance with the surgeon's physical input to footpedal 104, generating signals for controlling the two pumps.

In one embodiment, the present design may configure three operating zones relative to footpedal position as pressed by the surgeon, such as footpedal position one (FP1), footpedal position two (FP2), and footpedal position three (FP3). The present design may configure each operating zone for different MPC system operations, where, for example, FP1 may indicate the surgeon's need for irrigation, FP2 may indicate aspiration or vacuum, and FP3 may indicate the desired amount of power for driving the handpiece ultrasonic probe/needle. The surgeon may control each vacuum/pressure source by pressing the footpedal along a designated axis. For example, the system may generate footpedal signal pitch FP0 202 and yaw FP0 206 to indicate the initial or starting position for the pedal's pitch and yaw axes, or to indicate passing through these zero or neutral points. The footpedal 104 may generate footpedal signal pitch value 204 as well as yaw value 208 indicating the amount of pedal travel.

MPC system software 210 may process pitch and yaw signals received from footpedal 104 during the surgical procedure. MPC system software 210 may receive the footpedal values and may ramp up or ramp down the pumps, operating both pumps at the same time in some situations, to transition between pumps and offer desirable vacuum or pressure performance. For example, MPC system software 210 may enable surgeon operation of a peristaltic pump using the pitch axis of a dual linear footpedal and a venturi pump using the yaw axis. If the surgeon presses the dual linear footpedal to approximately 30 percent travel with zero yaw, a certain pressure will be produced by the peristaltic pump. MPC system software 210 recognizes that the surgeon turning her foot (in a yaw direction) indicates a desire to employ venturi pumping, and a smooth transition is desirable. Thus at a certain point MPC system software 210 may initiate venturi pumping to provide the ability to achieve the pressure produced by the peristaltic pump in a reasonable amount of time. Thus, two pumps can be running simultaneously to substantially maintain the pressure in the eye. This transition phenomenon and general operation of MPC system software 210 is discussed in more detail below and illustrated in FIGS. 3A, 3B, 4A, and 4B.

It is envisioned that a user (e.g. a surgeon) is capable of programming MPC system software 210 to run using preferred settings and/or programs. The user is capable of setting such parameters as defining the transition points between multiple pumps, whether particular features are automated or user controlled, etc.

Transition between pumps in this manner may effectively and efficiently maintain pressure in the eye. The present design may enable the surgeon to push and/or pull fluid and combine pushing with pulling of fluid through a single fluidic connection 225 between the instrument host 102 and handpiece 110.

The present design can switch the pathway for the vacuum source, such as a peristaltic pump and venturi pump, and combinations thereof, where one pathway is controlled by the relative footpedal pitch position and the second pathway is controlled by the relative footpedal yaw position. MPC system software 210 controls each vacuum source for operation with handpiece 110, where the combination of vacuum sources provides for aspiration. In this arrangement, MPC system software 210 provides the surgeon/operator the ability to maintain control of the flow based pump and simultaneously activate the vacuum based pump on demand.

The following examples presented herein are disclosed using a peristaltic pump and venturi pump for generating vacuum and/or flow from two different sources for purposes of simplifying the examples and illustrations. MPC system software 210 may apply a systematic algorithm, matrix, lookup tables, and/or user defined combinations thereof for providing ramping up and ramping down functionality to activate and deactivate the available pumps upon achieving known conditions. The software algorithm causes pressure to be maintained in the eye chamber when transitioning from a first pump to a second pump.

MPC system software 210 may determine a maximum allowable vacuum level based on actual vacuum, when using a vacuum based pump; or based on flow, when using a flow based pump and the handpiece needle is not occluded. MPC system software 210 may also take into account occlusions and vacuum/flow at time of transition and/or switch. Further, MPG system software 210 may also have safety features programmed to set various threshold parameters, such as, but not limited to vacuum level and flow rate. As the surgeon presses the footpedal into, for example, in aspirating mode, MPC system software 210 may determine the depth of travel from processing signals received from the footpedal 104. MPG system software 210 may translate the maximum amount of available footpedal travel in a desired footpedal zone or region into the maximum allowable vacuum level. The present design may enable the surgeon to select a value for maximum allowable linear vacuum, for example by selecting from an input parameter menu rendered by GUI host 101, such as 300 millimeters of mercury (mmHg).

It is also envisioned that various factors may be taken into consideration when transitioning, at the start of the transition, and/or when deciding to transition between multiple pumps, including, but not limited to flow rate, existence of an occlusion, and/or vacuum level. These various factors may be pre-programmed into the MPC system software 210 by a user or exist in the system as baseline requirements. Threshold parameters may be set to provide safety features.

In the example that follows, the present design is configured to operate the flow based pump using the footpedal pitch position signals and operate the vacuum based pump using the footpedal yaw position signals. In this example, the surgeon sets the maximum allowable linear vacuum to 300 mmHg. From this maximum, the software algorithm may calculate a maximum allowable vacuum of 150 mmHg when the footpedal depth of travel is positioned at 50% of the total travel through footpedal position FP2. While holding the footpedal at 50% travel into FP2 although any percent travel may be programmed, the surgeon may start the vacuum based pump by moving the pedal in the yaw direction of travel.

MPC system software 210 may receive and process signals generated by the footpedal 104 in the yaw direction or based on some other input provided by the surgeon. MPC system software 210 may determine the amount of vacuum resulting from yaw movement based on calculations from the following equation:

$$YAW_{vacuum} = ((\% \, Travel_{pitch} * MFBP) + [\text{the lesser of } (\% \, Travel_{yaw} * (MFBP * vacuum \, multiplier_{second \, pump})) \text{ and } (MVBP - MFBP)] \quad (1)$$

Example parameters in Equation (1) are maximum flow based pump pressure (MFBP)=300 mmHg, maximum vacuum based pump pressure (MVBP)=600 mmHg, pitch travel=50%, yaw travel=20%. The vacuum multiplier$_{second \, pump}$ governs the maximum vacuum when using the second pump. The vacuum multiplier$_{second \, pump}$ is based on the foot pedal travel at the Lime of engaging the second pump (e.g. vacuum level attained at that position or capable of attaining). A vacuum multiplier$_{second \, pump}$ of 1.5, indicating 20 percent yaw correlates to 30 percent of total available vacuum based pump pressure, yields a yaw vacuum value equal to:

$$YAW_{vacuum} = \\ ((50\% * 300 \text{ mmHg}) + [\text{the lesser of } (20\% * (300 \text{ mmHg} * 1.5)) \\ \text{and } (600 \text{ mmHg} - 300 \text{ mmHg}))$$

$$YAW_{vacuum} = ((150 \text{ mmHg}) + [\text{the lesser of } (90 \text{ mmHg}) \text{ or } (300 \text{ mmHg})] \\ = 240 \text{ mmHg}$$

The present design is configured to combine first pump for pitch pump) operation with second pump (or yaw pump) operation into a flow based system where, in this example, yaw vacuum is ramped up to 150 mmHg when the footpedal is at zero or neutral yaw, rather than starting yaw vacuum at 0 mmHg. As may be appreciated, if 150 mmHg is being produced by the pitch, asking the user to pull his foot back to the zero or neutral pitch position before engaging yaw and the second pump is undesirable, and also, simply shutting off the pitch pump and starting the yaw pump when yaw movement is detected is also unadvisable. Thus, the current system seeks to maintain the level of vacuum or pressure achieved at any time, enabling the surgeon to control a smooth transition from the first pump to the second pump.

Ramping up may continue to increase the flow rate until the switch or handoff from the first pump to the second pump is completed. MPC system software 210 may ramp down pressure to re-balance the inflow and outflow of fluid from the chamber. In this configuration, the surgeon may continue to operate the second pump until conditions indicate that, for example, a metered flow approach is better suited to continue the surgical procedure. For example, when switching back from a venturi pump mode to a peristaltic operating mode, MPC system software 210 may speed up the peristaltic pump to match the vacuum realized from venturi pump mode operation.

The present design may provide for tailoring of the ramp up and ramp down process responses during transitions and may include user configurable parameters, via GUI host 101 for example, where tailoring may involve configuring the system to provide for a more conservative or aggressive transition. One method for tailoring the response may involve changing the vacuum multiplier$_{second \, pump}$, set by the surgeon, to manage the system's aggressiveness, i.e. a transition from zero yaw to a larger yaw causes a jump in pressure. The surgeon may also change the desired vacuum multiplier$_{second \, pump}$, again representing the relationship between footpedal yaw and the resultant pressure for the yaw pump. In addition, the surgeon may use GUI host 101 to establish the width of each footpedal zone, e.g. FP1, FP2, FP3, etc.

Although the examples provided use the pitch axis of the dual linear footpedal 104 to control the peristaltic pump and the yaw axis to control the venturi pump, the present design may configure control for the second pump, such as a vacuum based pump, using the pitch axis and control for the first pump, such as a flow based pump, using the yaw axis. Alternate controllers may also be provided in addition to or in place of footpedal 104. The present design may also control multiple pumps of the same type.

Operational Example

Figure 3A:
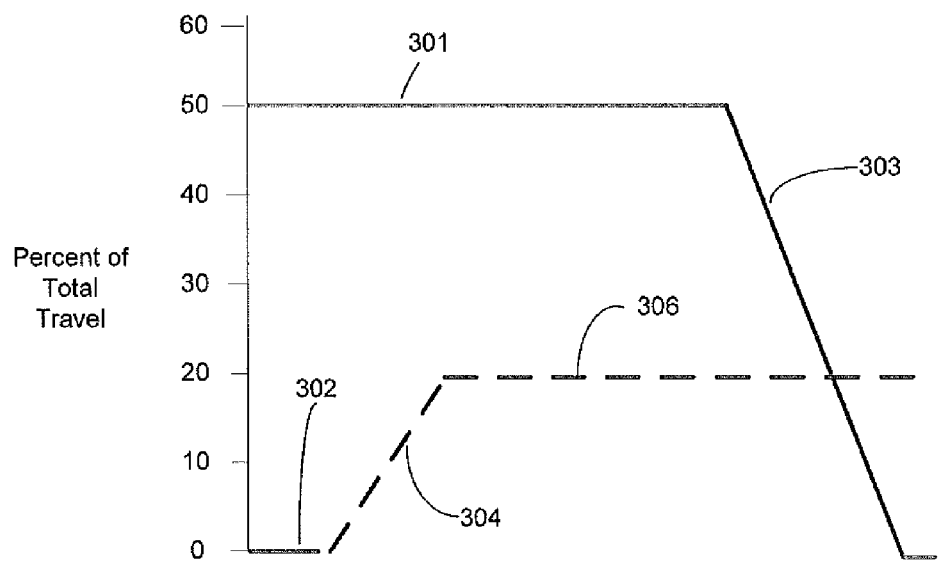
FIG. 3A is a graph illustrating the relationship between foot pedal positions pitch and yaw for transitions from the flow based pump to the vacuum based pump.
Figure 3B:
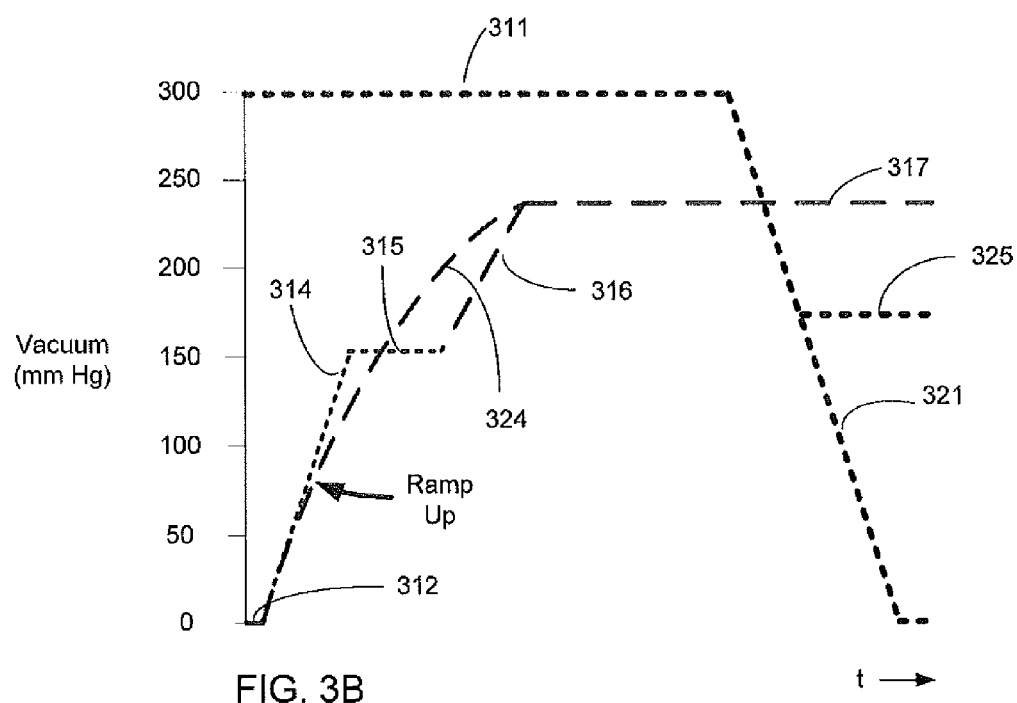
FIG. 3B is a graph illustrating the relationship between vacuum source operations for transitions from the flow based pump to the vacuum based pump.

FIGS. 3A and 3B illustrate the relationship between footpedal positions, pitch and yaw, and vacuum source operation for transitions from a first pump, here a flow based pump such as a peristaltic pump, to a second pump, here a vacuum based pump such as a venturi pump.

FIG. 3A is a graph illustrating the relationship between footpedal pitch and yaw for transitions from the flow based pump to the vacuum based pump. The graph illustrates the pitch axis footpedal position initially starting at and remaining at 50 percent travel at point 301. The yaw axis footpedal position is illustrated having an initial position of FP0, or neutral yaw, at point 302. The illustration depicts the surgeon adding a yaw axis pedal movement at point 304 when the surgeon decides to add the vacuum based pump and switch pumps. In this example, the surgeon yaws the pedal to twenty percent of total travel at line 306, keeping pitch at 50 percent, and continues to hold the footpedal steady. At a later point in time, the surgeon releases the footpedal in the pitch axis at point 303 and completes the transition from the first pump to the second pump.

FIG. 3B illustrates the relationship between vacuum sources for transitions from the flow based pump to the vacuum based pump corresponding to the two footpedal positions illustrated in FIG. 3A. The performance of FIG. 3B is dictated by MPC software system 210, which employs Equation (1) and other predetermined equations to translate footpedal position into pressure/vacuum performance. Initially, the first pump, here a peristaltic pump, is shown at a programmed maximum of 300 mmHg at line 311. The actual allowable vacuum is 150 mmHg resulting from pitch footpedal position 301, and the venturi pump is shown operating at 0 mmHg at line 312, corresponding to zero yaw.

When the surgeon moves the footpedal in the yaw direction, away from the FP0 or neutral yaw position, MPC software system 210 applies a ramp up function to increase the vacuum based flow at line 314 to a value where the vacuum based pump operation is ready to begin, namely line 315. Line 315 may be considered a "hold" level, i.e. a level at which pressure is held under the circumstances when the second pump has just been turned on but the footpedal is still moving. Note that alternate operation may be provided, such as starting the pump and simply attempting to achieve the footpedal commanded value, shown by alternate line 324. The application of footpedal movement is shown to be clean and linear, and in practice it may be nonlinear or materially different from the curve shown.

Based on the yaw pedal position at twenty percent, as shown in FIG. 3A, MPC software system 210 raises the vacuum at line 316 to a transition value at line 317. When the surgeon releases the footpedal from being pressed in the pitch axis, or returns to the zero or neutral pitch position, the peristaltic vacuum pressure is reduced as shown by line 321. Alternately, the first/peristaltic pump may be reduced to a desired level, either a hard level or a computed level, where it awaits further engagement such as pressing of the footpedal in the pitch axis from the zero or neutral point. One alternate position, when the footpedal of FIG. 3A is reduced to zero, is to maintain the peristaltic pump unengaged but continuing to operate at level 325, i.e. a level of 175 mmHg.

Thus the resultant pressure encountered follows line 311 until it reaches line 317, and the pressure of line 317, approximately 240 mmHg, is maintained. In the meantime, the non-utilized pump remains running in the "background" awaiting engagement and operation using the footpedal.

Figure 4A:
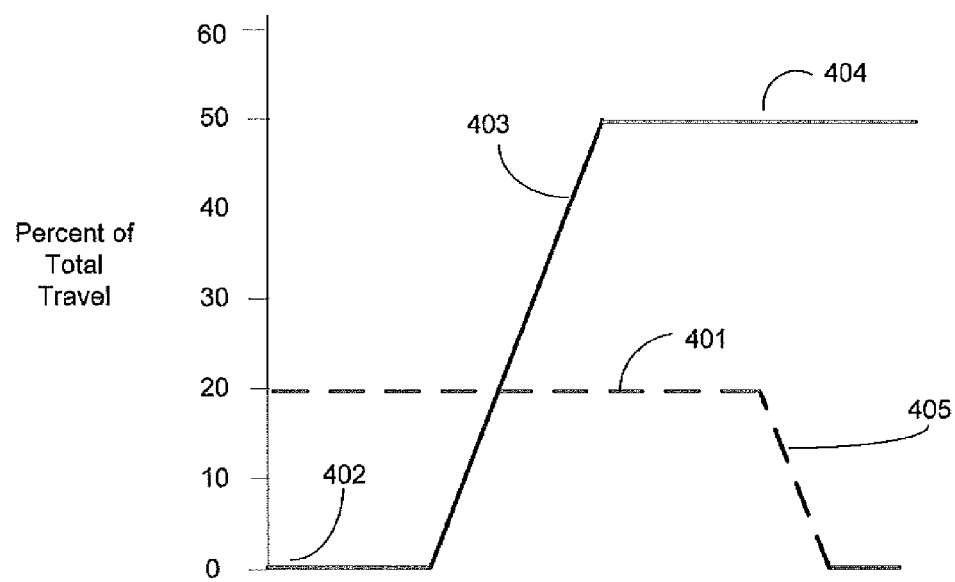
FIG. 4A is a graph illustrating the relationship between foot pedal positions pitch and yaw for transitions from the vacuum based pump to the flow based pump.
Figure 4B:
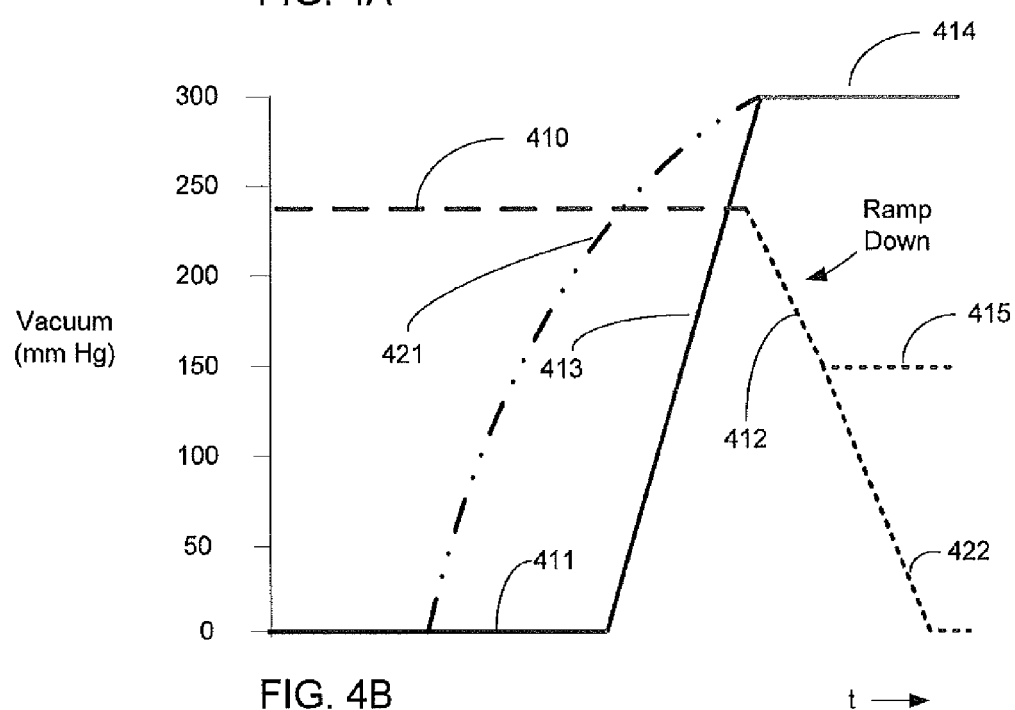
FIG. 4B is a graph illustrating the relationship between vacuum source contributions for transitions from the vacuum based pump to the flow based pump.

FIGS. 4A and 4B are graphs illustrating the relationship between footpedal positions, pitch and yaw, and vacuum source operation for transitions from the second pump, such as a vacuum based pump, to the first pump, such as the flow based pump.

FIG. 4A is a graph illustrating the relationship between footpedal positions pitch and yaw for transitions from the second pump to the first pump. The graph illustrates the yaw axis footpedal position initially starting at and remaining at 20 percent travel at line 401. The pitch axis footpedal position is illustrated having an initial position of FP0 at line 402. The illustration depicts the surgeon adding a pitch axis pedal movement at line 403 where the surgeon decides to add the flow based pump in the course of switching pumps. In this example, the surgeon has applied pitch to the footpedal to fifty percent of total travel at line 404 and holds the pedal steady. The surgeon later releases the footpedal in the yaw axis at line 405 and completes the transition back from the second pump to the first pump.

FIG. 4B is a graph illustrating the relationship between vacuum source contributions for transitions from the second pump to the first pump corresponding to the footpedal positions illustrated in FIG. 4A. Initially, the second pump, here a venturi pump, operates at 240 mmHg at line 410, and the first: pump, here a peristaltic pump, operates at 0 mmHg at line 411.

When the surgeon begins to apply pressure in the pitch direction in addition to the 20 percent yaw direction as shown in FIG. 4A, the first pump may not act for a predetermined period of time as shown in FIG. 4B by lines 411 and 413, or may begin to act immediately as shown by line 421. Other combinations of movement in the second axis may be provided depending on surgeon desires and programming of MPC system software 210.

After the surgeon moves the footpedal in the pitch direction, MPC system software 210 may apply a ramp down function to decrease the vacuum based flow at line 412, where the first pump operation is increased to 300 mmHg at line 413. With the pitch pedal position at fifty percent, the present design may reduce the vacuum by a fixed amount or some percentage depending on circumstances as shown by line 412, and this reduction is determined by MPC system software 210. When the surgeon releases the footpedal in the yaw axis, the peristaltic vacuum is increased to a final amount at line 414.

Thus the resultant pressure encountered follows line 410 until it reaches line 413, and the pressure increases along line 413 to line 414, where approximately 300 mmHg is achieved. If the performance of line 421 is called for, performance follows from line 410 to line 421 and finally line 414. Again, the non-utilized pump remains running in the "background" awaiting engagement and operation using the footpedal, as shown by line 415. Alternately, the non-utilized pump may be run down to a lower value or even zero, as shown by line 422.

Figure 5:
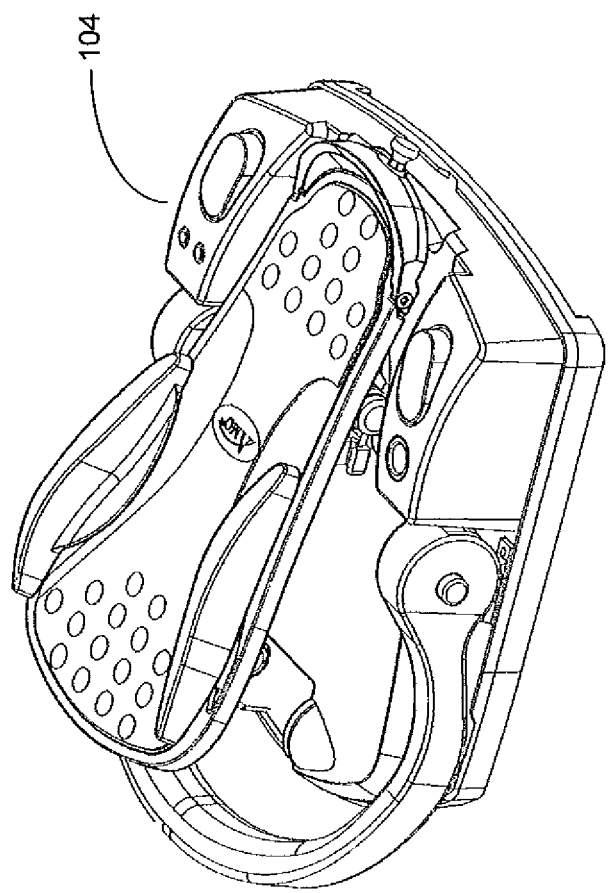
FIG. 5 illustrates an exemplary dual linear footpedal for use in accordance with an aspect of the present design.

FIG. 5 illustrates an exemplary dual linear footpedal that may be employed in accordance with the current design. In the embodiment illustrated, MPC system software 210 receives one or more control signals from footpedal 104. The control signals generated by footpedal 104 may report the status of various physical and virtual switches contained within footpedal 104 or provided by footpedal 104, or other parameters such as yaw linear position and pitch linear position.

The footpedal firmware, not shown, within the footpedal reads and processes the switch inputs. The footpedal firmware may produce signals resulting from the button and switch positions triggered on footpedal 104. The signals are ultimately destined for instrument host 102 executing MPC system software 210. Signals may include but are not limited to position of a footpedal, such as left heel, center heel, right heel, pitch safety detect, pitch, and yaw positions; button pushes or "stomp" values, or other appropriate states in the case of a footpedal. Moreover, predefined footpedal positions FP0, FP1, FP2, etc. (FPn) may be communicated. For example, pitch FP0 202 and yaw FP0 206 may be communicated when the footpedal slave subsystem becomes connected and footpedal 104 is in a neutral or zero position.

Footpedal 104 may be connected to instrument host 102 using a fixed wire or wireless, e.g. Bluetooth®, connection for the purpose of transmitting signals.

Figure 6:
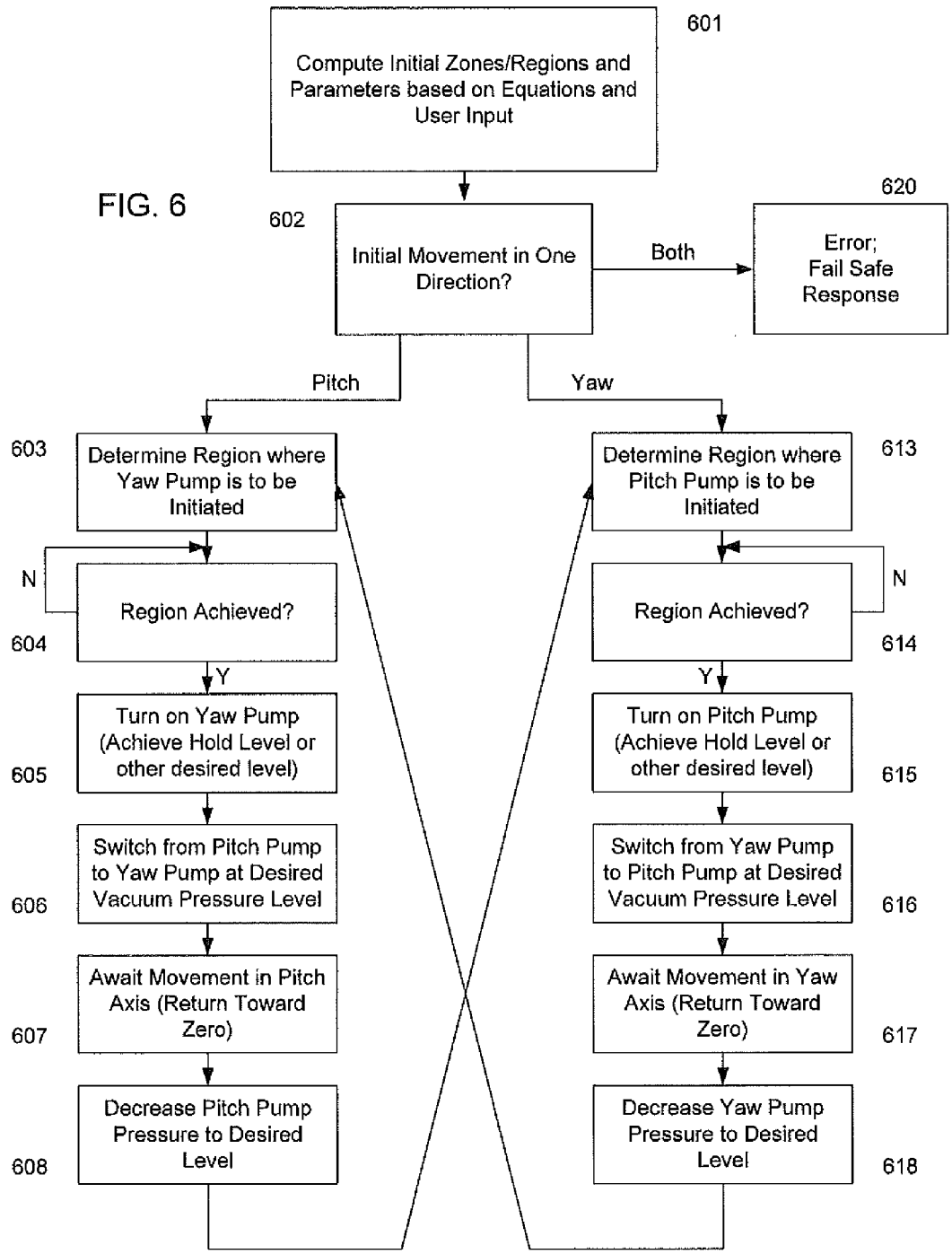
FIG. 6 is a flowchart illustrating general operation of the system software to control transitions between the two pumps.

FIG. 6 illustrates a broad general flowchart of pertinent operation of MPC system software 210, the results of which may be the pressure values depicted in FIGS. 3B and 4B. Point 601 illustrates collection of all pertinent data and parameters to employ, for example, surgeon settings and desires, maximum and minimum expected and allowed values and settings, and so forth. MPC system software 210 initially determines movement in one direction or the other at point 602. In the case where movement in both directions is sensed, the system may (1) provide a fail-safe response or responses, such as issuing a warning or not operating either pump, or ignoring one axis, or (2) provide the desired pump levels for both pumps at the same time, such that a surgeon may start a procedure by engaging both the pitch and yaw direction, wherein the pumps run at the same time. Although only the first option is illustrated in FIG. 6 at 602, the second is also an option at 602.

If movement in the pitch direction is detected, then based on the amount of total pitch travel, the system may determine the point or footpedal position at which a second pump is to be turned on at point 603. If the region is achieved at point 604, the second pump is turned on at point 605, and the second pump is to operate as desired, such as achieving a "hold" level as shown in FIG. 3B at line 315, or simply attempting to achieve the pump level commanded as shown by line 324 in FIG. 3B. The system may then await movement of the footpedal back toward neutral in the pitch axis or movement in the yaw axis from the current location of the footpedal, representing an indication that the surgeon desires second pump operation.

Point 606 indicates switching between pumps at the desired or computed pressure level(s). Awaiting release of the footpedal in the pitch axis is shown at point 607, although 607 may also be awaiting movement in the yaw axis. The result of either actions is the release of first pump pressure and a decrease in first pump pressure to a desired level, such as a hold or computed level, at point 608. Operation then transitions to the other axis, and operation of the pump in the other axis (e.g. yaw) and monitoring of the pump in this axis (e.g. pitch).

Action and operation in the yaw axis, indicating initial yaw movement, occurs in a similar manner to the pitch axis. Point 613 determines the region where the pitch pump is to be turned on and point 614 monitors whether that pitch pump initiation region has been achieved. If so, point 615 activates the pitch pump and may hold the pitch pump, such as the peristaltic pump, at a desired hold level or attempts to attain the desired pressure level, or operates in any other manner requested or established. Point 616 switches between the pumps at the desired pressure level, while point 617 awaits movement in the yaw axis back to the yaw zero or neutral point or movement in the pitch axis from the current location of the footpedal. Point 618 decreases the second pump pressure accordingly, back to a predetermined or calculated level, and operation goes to the pitch axis on completion of transition.

As used in FIG. 6, there is provided a "pitch" or first pump and a "yaw" or second pump. These terms are provided for illustrative purposes and may represent the aforementioned peristaltic and/or venturi pumps and axes of control may be reversed, but in essence one pump is controlled based at least in part on input along one axis while the second pump is controlled based at least in part on input received along the second axis. The terms yaw and pitch in FIG. 6 are therefore not intended to be limiting.

In this manner, the user can keep transitioning pumps until the footpedal is released, a situation monitored but not shown in FIG. 6 that results in both pumps being turned off.

Thus the present design provides a method for operating two pressure sources (pumps), comprising receiving pressure from a first pressure source using a multiple channel adjustment apparatus, such as a dual axis footpedal, configured to operate with the first pressure source to provide pressure at a first pressure level based on a first channel state of the multiple channel adjustment apparatus. The method further includes transitioning from receiving pressure from the first pressure source to receiving pressure from a second pressure source at a desirable pressure level using the multiple channel adjustment apparatus configured to operate with the second pressure source to provide pressure at a second pressure level based on a second channel state of the multiple channel adjustment apparatus.

The design may also be considered to provide a method for delivering vacuum, comprising controlling a first vacuum source using a first signal received from a dual axis device indicating a first axis position, controlling a second vacuum source with a second signal using a second signal received from the dual axis device indicating a second axis position, and switching from the first vacuum source to the second vacuum source based on the second axis position.

The present design illustrates an apparatus for controlling vacuum pressure, comprising a multiple axis controller, such as a dual axis footpedal operable in pitch and yaw, a processing apparatus, such as an instrument host running software, configured to receive multiple axis data from the multiple axis controller. The apparatus also includes a first vacuum pressure source configured to provide vacuum pressure at a first vacuum pressure level based on a first axis state of the multiple axis controller and a second vacuum pressure source configured to provide vacuum pressure at a second vacuum pressure level based on a second axis state of the multiple axis controller. The processing apparatus switches between the first vacuum pressure source and the second vacuum pressure source based on the first axis state and the second axis state of the multiple axis controller.

In short, the present design may provide for independent and/or dependent control over two separate pumps configured to provide efficient transitions when switching between, for example, flow based and vacuum based aspiration operation, and vice versa, while affording acceptable chamber stability. The dual-linear or dual axis footpedal arrangement may afford the surgeon to realize vacuum on demand functionality and a method to moderate maximum vacuum based on transition to a flow based pump when controlling the present design.

The design presented herein and the specific aspects illustrated are meant not to be limiting, but may include alternate components while still incorporating the teachings and benefits of the invention. While the invention has thus been described in connection with specific embodiments thereof, it will be understood that the invention is capable of further modifications. This application is intended to cover any variations, uses or adaptations of the invention following, in general, the principles of the invention, and including such departures from the present disclosure as come within known and customary practice within the art to which the invention pertains.

The foregoing description of specific embodiments reveals the general nature of the disclosure sufficiently that others can, by applying current knowledge, readily modify and/or adapt the system and method for various applications without departing from the general concept. Therefore, such adaptations and modifications are within the meaning and range of equivalents of the disclosed embodiments. The phraseology or terminology employed herein is for the purpose of description and not of limitation.

What is claimed is:

1. A method for operating at least two pumps, comprising:
   activating a first pump using a multiple channel adjustment apparatus configured to operate with the first pump to provide nonzero fluid pressure at a first nonzero fluid pressure level based on a first channel state of the multiple channel adjustment apparatus; and
   transitioning from the first pump providing nonzero fluid pressure at the first nonzero fluid pressure level to a second pump providing nonzero fluid pressure at a second nonzero fluid pressure level using the multiple channel adjustment apparatus based on the first channel state, wherein the transitioning includes applying ramping functions when transitioning between the first pump and the second pump.

2. The method of claim 1, further comprising operating the second pump to a desired nonzero fluid pressure level prior to said transitioning.

3. The method of claim 1, wherein transitioning from the first pump providing nonzero fluid pressure at the first nonzero fluid pressure level to a second pump providing nonzero fluid pressure at a second nonzero fluid pressure level comprises:
   providing nonzero fluid pressure from the first pump at the first nonzero fluid pressure level;
   operating the second pump at the second nonzero fluid pressure level; and
   transitioning from providing nonzero fluid pressure from the first pump at the first nonzero fluid pressure level to providing pressure from the second pump at the second nonzero fluid pressure level.

4. The method of claim 1, further comprising decreasing operation of the first pump to a predetermined level after said transitioning.

5. The method claim 1, wherein the multiple channel adjustment apparatus comprises a dual channel control apparatus having movement capabilities in two axes.

6. The method of claim 5, wherein the dual channel control apparatus comprises a dual axis footpedal.

7. The method of claim 1, wherein nonzero pressure levels received from the first pump and the second pump are based on data received from the multiple channel adjustment apparatus and settings established by a user.

8. The method of claim 1, wherein at least one of the first nonzero pressure level and second nonzero pressure level comprises a first vacuum level.

9. The method of claim 1, wherein at least one of the first nonzero pressure level and second nonzero pressure level comprises a positive pressure level.

10. The method of claim 1, wherein providing nonzero fluid pressure at at least one of the first nonzero pressure level and second nonzero pressure level causes fluid to be aspirated from an eye.

11. The method of claim 1, wherein providing nonzero fluid pressure at at least one of the first nonzero pressure level and second nonzero pressure level causes an eye to be irrigated with pumped fluid.

12. The method of claim 1, wherein the transition is further based on a second channel state of the multiple channel adjustment apparatus.

13. A method for delivering nonzero pressure, comprising:
   controlling a first pump using a first signal received from a dual axis device indicating a first axis position;
   controlling a second pump using a second signal received from the dual axis device indicating a second axis position; and
   switching from the first pump to the second pump based on the second axis position wherein the switching includes applying ramping functions when switching between the first pump and the second pump.

14. The method of claim 13, further comprising deactivating the first pump from concurrent operation with the second pump by applying a ramp down control function subsequent to switching from the first pump to the second pump.

15. The method of claim 13, further comprising, after switching from the first pump to the second pump, subsequently switching from the second pump to the first pump based on the first axis position.

16. The method of claim 13, wherein controlling the second pump comprises operating the second pump to a desired nonzero fluid pressure level and refraining from employing the second pump at the desired nonzero fluid pressure level prior to said switching.

17. The method of claim 13, wherein switching from the first pump to the second pump based on the second axis position comprises:
   causing the first pump to provide first nonzero fluid pressure at a first nonzero fluid pressure value;
   operating the second pump at a second nonzero fluid pressure value based on the second axis position; and
   switching from the first pump and the first nonzero fluid pressure value to the second pump operating at the second nonzero fluid pressure value.

18. The method of claim 13, further comprising decreasing operation of the first pump to a predetermined level after said switching based on the first axis position.

19. The method of claim 13, wherein the dual axis device comprises a dual axis footpedal.

20. The method of claim 13, wherein nonzero pressure levels received from the first pump and the second pump are based on data received from the dual axis device and settings established by a user.

21. An apparatus for controlling vacuum pressure, comprising:
   a multiple axis controller;
   a processing apparatus configured to receive multiple axis data from the multiple axis controller;
   a first pump configured to provide nonzero fluid pressure at a first nonzero fluid pressure level based on a first axis state of the multiple axis controller; and
   a second pump configured to provide nonzero fluid pressure at a second nonzero fluid pressure level based on a second axis state of the multiple axis controller;
   wherein the processing apparatus is further configured to switch between the first pump and the second pump based on the first axis state and the second axis state of the multiple axis controller, wherein the processing apparatus provides ramping functions when switching between the first pump and the second pump.

22. The apparatus of claim 21, wherein the processing apparatus is further configured to deactivate the first pump from concurrent operation with the second pump by applying a ramp down control function after switching from the first pump to the second pump.

23. The apparatus of claim 21, wherein the processing apparatus switches from the first pump to the second pump based on first axis data received from the multiple axis controller.

24. The apparatus of claim 21, wherein the second pump is configured to operate to a desired level and the apparatus refrains from employing nonzero fluid pressure at a second nonzero fluid pressure level prior to the processing apparatus switching.

25. The apparatus of claim 24, wherein switching comprises switching from the first pump operating at the first nonzero fluid pressure value to the second pump operating at the second nonzero vacuum pressure value.

26. The apparatus of claim 21, wherein the multiple axis controller comprises a dual axis footpedal.

27. The apparatus of claim 21, wherein switching is based on data received from the dual axis controller and settings established by a user.

28. The apparatus of claim 21, wherein the processor apparatus comprises an instrument host running a software application configured to switch between the first pump and the second pump based on the first axis state and the second axis state of the multiple axis controller.

* * * * *